United States Patent
Benin et al.

(10) Patent No.: US 9,694,353 B2
(45) Date of Patent: Jul. 4, 2017

(54) MOLECULAR SIEVE SSZ-90, ITS SYNTHESIS AND USE

(71) Applicant: Chevron U.S.A. Inc., San Ramon, CA (US)

(72) Inventors: Annabelle Benin, Richmond, CA (US); Stacey Ian Zones, San Francisco, CA (US); Cong-Yan Chen, Kensington, CA (US); Dan Xie, Richmond, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 167 days.

(21) Appl. No.: 14/877,457

(22) Filed: Oct. 7, 2015

(65) Prior Publication Data

US 2017/0100711 A1    Apr. 13, 2017

(51) Int. Cl.
| | |
|---|---|
| *C01B 39/54* | (2006.01) |
| *B01J 29/84* | (2006.01) |
| *B01J 29/85* | (2006.01) |
| *C07C 4/06* | (2006.01) |
| *C01B 39/48* | (2006.01) |

(52) U.S. Cl.
CPC .............. *B01J 29/85* (2013.01); *B01J 29/84* (2013.01); *C01B 39/54* (2013.01); *C07C 4/06* (2013.01); *C01B 39/48* (2013.01); *C07C 2529/74* (2013.01)

(58) Field of Classification Search
CPC  C01B 39/48; C01B 39/54; B01J 29/84; B01J 29/85
See application file for complete search history.

(56) References Cited

U.S. PATENT DOCUMENTS

| | | | |
|---|---|---|---|
| 7,108,843 B2 * | 9/2006 | Zones | C01B 37/007 423/329.1 |
| 7,157,075 B1 * | 1/2007 | Burton, Jr. | C01B 39/48 423/705 |

(Continued)

FOREIGN PATENT DOCUMENTS

| | | | |
|---|---|---|---|
| FR | 2674858 A1 * | 10/1992 | B01J 29/82 |
| JP | 2153817 A * | 6/1990 | |
| WO | WO0122579 A3 * | 10/2008 | |

OTHER PUBLICATIONS

P.A. Wright, R.H. Jones, S. Natarajan, R.G. Bell, J. Chen, M.B. Hursthouse and J.M. Thomas "Synthesis and Structure of a Novel Large-pore Microporous Magnesiun-containing Aluminophosphate (DAF-1)" J. Chem. Soc. Chem. Commun. 1993, 633-635.

(Continued)

Primary Examiner — David M Brunsman
(74) Attorney, Agent, or Firm — Terrence M. Flaherty

(57) ABSTRACT

A new crystalline zinc (silico)aluminophosphate molecular sieve designated SSZ-90 is disclosed. SSZ-90 is isostructural with the DFO framework type and is synthesized using an ionic liquid as both the solvent and the structure directing agent. The ionic liquid [$Q^+A^-$] comprises a cation ($Q^+$) selected from the group consisting of 1,3-diisopropylimidazolium, 1,3-diisobutylimidazolium, and 1-isopropyl-3-isobutylimidazolium and an anion ($A^-$) which is not detrimental to the formation of the molecular sieve.

17 Claims, 7 Drawing Sheets

(56) References Cited

U.S. PATENT DOCUMENTS 7,527,782 B2 * 5/2009 Corma .................... B01J 29/70
423/702
2013/0266785 A1 * 10/2013 Chen ........................ B01J 20/18
428/219

OTHER PUBLICATIONS

P.A. Wright, C. Sayag, F. Rey, D.W. Lewis, J.D. Gale, S. Natarajan and J.M. Thomas "Synthesis, Characterisation and Catalytic Performance of the Solid Acid DAF-1" J. Chem. Soc., Faraday Trans., 1995, 91, 3537-3547.

S.J. Thomson and R.F. Howe "Spectroscopic Studies of a Magnesium Substituted Microporous Aluminophosphate DAF-1" Stud. Surf. Sci. Catal. 1997, 105, 447-454.

G. Muncaster, G. Sankar, C.R.A. Catlow, J.M. Thomas, R.G. Bell, P.A. Wright, S. Coles, S.J. Teat, W. Clegg and W. Reeve "An in Situ Microcrystal X-ray Diffraction Study of the Synthetic Aluminophosphate Zeotypes DAF-1 and CoAPSO-44" Chem. Mater. 1999, 11, 158-163.

E.R. Cooper, C.D. Andrews, P.S.Wheatley, P.B. Webb, P. Wormald and R.E. Morris "A New Methodology for Zeolite Analogue Synthesis Using Ionic Liquids as Solvent and Template" Stud. Surf. Sci. Catal. 2005,158, 247-254.

R.E. Morris "Ionothermal Synthesis-Ionic Liquids as Functional Solvents in the Preparation of Crystalline Materials" Chem. Commun. 2009, 2990-2998.

R.H. Archer, J.R. Carpenter, S-J. Hwang, A.W. Burton, C-Y. Chen, S.I. Zones and M.E. Davis "Physicochemical Properties and Catalytic Behavior of the Molecular Sieve SSZ-70" Chem. Mater. 2010, 22, 2563-2572.

J. Li, J. Yu and R. Xu "Progess in Heteroatom-Containing Aluminophosphate Molecular Sieves" Proc. R. Soc. A 2012, 468, 1955-1967.

* cited by examiner

MOLECULAR SIEVE SSZ-90, ITS SYNTHESIS AND USE

TECHNICAL FIELD

This disclosure is directed to a new crystalline zinc (silico)aluminophosphate molecular sieve designated SSZ-90, a method for preparing the molecular sieve, and uses for the molecular sieve.

BACKGROUND

Crystalline molecular sieves have a three-dimensional, four-connected framework structure of corner-sharing [TO$_4$] tetrahedral units, where T is any tetrahedrally coordinated cation. Among the known forms of molecular sieves are aluminosilicates, which contain a three-dimensional microporous crystal framework structure of [SiO$_4$] and [AlO$_4$] corner-sharing tetrahedral units; aluminophosphates, in which the framework structure is composed of [AlO$_4$] and [PO$_4$] corner-sharing tetrahedral units; and metalloaluminophosphates, in which the framework structure is composed of [MO$_4$], [AlO$_4$] and [PO$_4$] corner-sharing tetrahedral units. The metal (M) is usually selected from the group consisting of silicon, magnesium, zinc, iron, cobalt, nickel, manganese, chromium, and combinations thereof.

Molecular sieves have been classified by the Structure Commission of the International Zeolite Association (IZA) according to the rules of the IUPAC Commission on Zeolite Nomenclature. According to this classification, framework-type zeolite and zeolite-type molecular sieves, for which a structure has been established, are assigned a three-letter code and are described in the "*Atlas of Zeolite Framework Types*," Sixth Revised Edition, Elsevier, 2007.

One known molecular sieve for which a structure has been established is the material designated as DFO, which is a molecular sieve having two parallel channels of circular pore apertures of about 6.1 Å and 7.5 Å respectively with interconnecting 8- and 10-ring channels. The known member of the DFO framework type is DAF-1, a magnesium-substituted aluminophosphate.

P. A. Wright et al. (*J. Chem. Soc., Chem. Commun.* 1993, 633-35) disclose molecular sieve DAF-1 and its synthesis under hydrothermal conditions using a decamethonium cation as a structure directing agent.

It has now been found that crystalline zinc (silico)aluminophosphate molecular sieves isostructural with the DFO framework type can be synthesized using a 1,3-dialkylimidazolium-based ionic liquid as both the solvent and the structure directing agent.

SUMMARY

The present disclosure is directed to a family of crystalline zinc (silico)aluminophosphate molecular sieves with unique properties, referred to herein as "molecular sieve SSZ-90" or simply "SSZ-90."

In one aspect, there is provided a crystalline molecular sieve comprising [ZnO$_4$], [AlO$_4$] and [PO$_4$] corner-sharing tetrahedral units and is isostructural with the DFO framework type. In its as-synthesized form, the molecular sieve has the X-ray diffraction lines of Table 2.

In one aspect, there is provided a method for preparing a crystalline molecular sieve comprising [ZnO$_4$], [AlO$_4$] and [PO$_4$] corner-sharing tetrahedral units and having the DFO framework type by: (a) preparing a reaction mixture containing (1) at least one source of zinc; (2) optionally, at least one source of silicon; (3) at least one source of aluminum; (4) at least one source of phosphorus; (5) fluoride ions; and (6) an ionic liquid comprising (i) a cation selected from the group consisting of 1,3-diisopropylimidazolium, 1,3-diisobutylimidazolium, and 1-isopropyl-3-isobutylimidazolium and (ii) an anion which is not detrimental to the formation of the molecular sieve; and (b) maintaining the reaction mixture under crystallization conditions sufficient to form crystals of the molecular sieve.

In one aspect, there is provided a crystalline molecular sieve having the DFO framework type and which, in its as-synthesized form and on an anhydrous basis, is represented by the empirical formula:

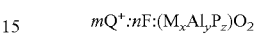

wherein: (1) Q$^+$ represents a cation selected from the group consisting of 1,3-diisopropylimidazolium, 1,3-diisobutylimidazolium, and 1-isopropyl-3-isobutylimidazolium; (2) m is the number of moles of Q$^+$ per mole of (M$_x$Al$_y$P$_z$)O$_2$, and 0<m≤1; (3) n is the number of moles of fluoride ions per mole of (M$_x$Al$_y$P$_z$)O$_2$, and 0<n≤1; (4) M is a metal selected from zinc or a combination of zinc and silicon; (5) x is the mole fraction of M as tetrahedral oxides, and 0<x≤0.5; (6) y is the mole fraction of Al as tetrahedral oxides, and y>0; (7) z is the mole fraction of P as tetrahedral oxides, and z>0; and (8) x+y+z=1.

In one aspect, there is provided a process for converting a feedstock comprising an organic compound to a conversion product which comprises the step of contacting the feedstock with a catalyst at organic compound conversion conditions, the catalyst comprising an active form of the molecular sieve described herein.

DETAILED DESCRIPTION

Introduction

Figure 1:
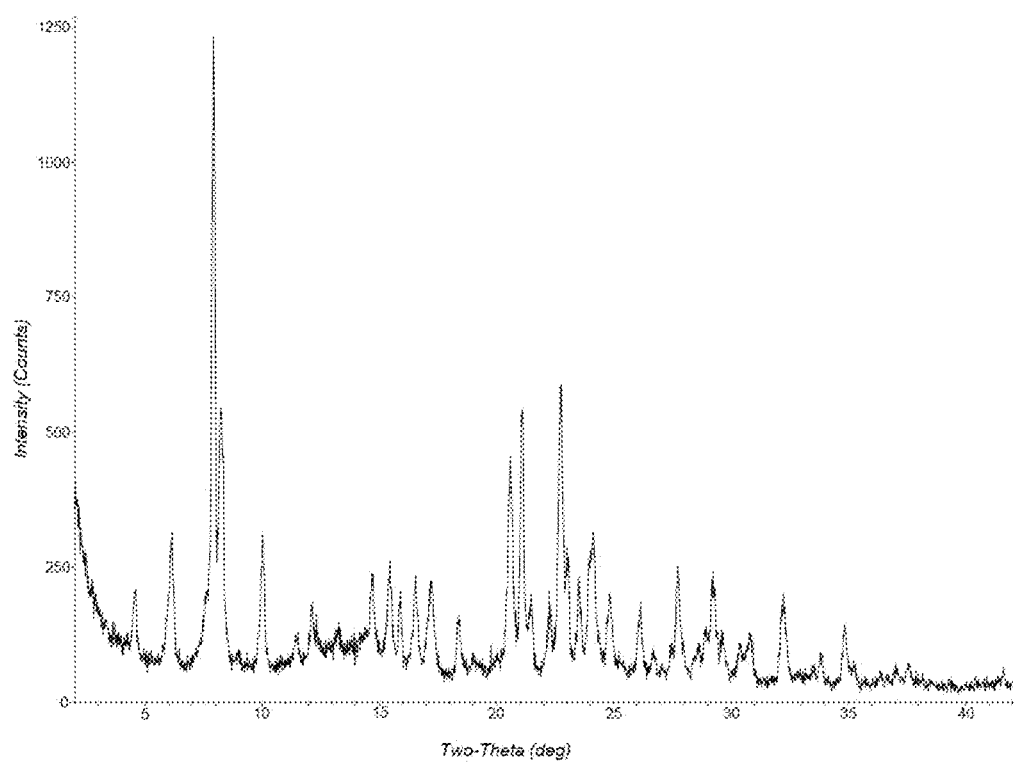
FIG. 1 is a powder X-ray diffraction (XRD) pattern of the as-synthesized ZnAPO molecular sieve prepared in Example 2.

The following terms and abbreviations will be used throughout the specification and will have the following meanings unless otherwise indicated.

The term "ionic liquid" refers to an organic salt which is liquid at temperatures below 100° C., e.g., at temperatures below 50° C. All data are based on atmospheric pressure (1 bar).

The term "framework type" is used in the sense described in the "*Atlas of Zeolite Framework Types,*" Sixth Revised Edition, Elsevier, 2007.

"Zinc aluminophosphate" is abbreviated as ZnAPO.

"Zinc silicoaluminophosphate" is abbreviated as ZnSAPO.

"Magic Angle Spinning Nuclear Magnetic Resonance" is abbreviated as MAS NMR

"Cross-Polarization Magic Angle Spinning Nuclear Magnetic Resonance" is abbreviated as CPMAS NMR, Reaction Mixture In general, molecular sieve SSZ-90 is prepared by: (a) preparing a reaction mixture containing: (1) at least one source of zinc; (2) optionally, at least one source of silicon; (3) at least one source of aluminum; (4) at least one source of phosphorus; (5) fluoride ions; and (6) an ionic liquid comprising (i) a cation selected from the group consisting of 1,3-diisopropylimidazolium, 1,3-diisobutylimidazolium, and 1-isopropyl-3-isobutylimidazolium and (ii) an anion which is not detrimental to the formation of the molecular sieve; and (b) subjecting the reaction mixture to crystallization conditions sufficient to form crystals of the molecular sieve.

The composition of the reaction mixture from which the molecular sieve is formed, in terms of mole ratios, is identified in Table 1 below:

TABLE 1

|  | Broad | Exemplary |
|---|---|---|
| $ZnO/Al_2O_3$ | 0.05 to 1.5 | 0.1 to 1.0 |
| $SiO_2/Al_2O_3$ | 0 to 0.90 | 0.05 to 0.70 |
| $P_2O_5/Al_2O_3$ | 0.50 to 1.50 | 0.80 to 1.20 |
| $F/Al_2O_3$ | 0.25 to 0.75 | 0.25 to 0.75 |
| $[Q^+A^-]/Al_2O_3$ | 5 to 100 | 5 to 40 | wherein $[Q+A^-]$ represents an ionic liquid comprising a cation ($Q^+$) selected from the group consisting of 1,3-diisopropylimidazolium, 1,3-diisobutylimidazolium, and 1-isopropyl-3-isobutylimidazolium; and an anion ($A^-$) which is not detrimental to the formation of the molecular sieve. Representative anions may include halides (fluoride, chloride, bromide, iodide), acetates, phosphates, phosphinates, aluminates, borates, sulfates, sulfonates, imides, amides, and cyanates.

Suitable zinc sources include zinc salts, such as halides, nitrates, sulfates, and carboxylates.

Suitable sources of silicon include silicates (e.g., tetraalkyl orthosilicates), fumed silica, and colloidal silica.

Suitable sources of aluminum include aluminum alkoxides (e.g., aluminum isopropoxide), precipitated aluminas, aluminum hydroxide, aluminum salts and alumina sols.

A suitable phosphorus source is phosphoric acid.

Suitable fluoride sources include hydrogen fluoride and ammonium fluoride.

Optionally, the reaction mixture may also include seeds of a molecular sieve material, such as SSZ-90 from a previous synthesis, e.g., in an amount of from 0.1 to 10 wt. % or from 0.5 to 5 wt. % of the reaction mixture.

For each embodiment described herein, the molecular sieve reaction mixture can be supplied by more than one source. Also, two or more reaction components can be provided by one source.

The reaction mixture can be prepared either batch wise or continuously. Crystal size, morphology and crystallization time of the molecular sieve described herein can vary with the nature of the reaction mixture and the synthesis conditions.

Crystallization and Post-Synthesis Treatment

The synthesis of (metallo)aluminophosphate molecular sieves is normally conducted by initially producing a reaction mixture comprising water, an organic structure directing agent (typically a nitrogen-containing organic base, such as a quaternary ammonium salt or hydroxide), an aluminum oxide, phosphoric acid and, optionally, a source of silicon or other metal. The resulting gel mixture is then subjected to hydrothermal conditions (i.e., temperatures above 100° C. and pressures above atmospheric pressure) in a sealed vessel to induce crystallization. The crystalline product is then recovered by filtration or centrifugation.

In contrast to conventional hydrothermal synthesis where the solvent is water, molecular sieve SSZ-90 is prepared by ionothermal synthesis where an ionic liquid is used as both the solvent and the structure directing agent in the formation of solids.

Crystallization of the molecular sieve SSZ-90 can be carried at either static or stirred conditions in a suitable reactor vessel, such as, for example, polypropylene jar or Teflon-lined or stainless steel autoclaves, at a temperature of from 100° C. to 200° C. (e.g., from 140° C. to 180° C.) for a time sufficient for crystallization to occur at the temperature used (e.g., from 1 to 20 days, or from 2 to 10 days).

Once the molecular sieve crystals have formed, the solid product is separated from the reaction mixture by standard mechanical separation techniques such as filtration. The crystals are water-washed and then dried to obtain the as-synthesized molecular sieve crystals. The drying step can be performed at atmospheric pressure or under vacuum. The drying step is typically performed at a temperature of less than 200° C.

Optionally, the ionic liquid solvent can be recovered from the reaction mixture using any of a variety of techniques (e.g., solvent extraction, decantation) for subsequent use.

As a result of the crystallization process, the recovered crystalline molecular sieve product contains within its pore structure at least a portion of the structure directing agent used in the synthesis.

Structure directing agents are typically removed by thermal treatment (e.g., calcination) in an oxidative atmosphere (e.g., air, gas with an oxygen partial pressure of greater than 0 kPa) at temperatures ranging from 300° C. to 800° C. for periods of time ranging from 1 to 48 hours, or more. However, some microporous crystalline materials are not thermally stable, and calcination processes cannot be used to remove the organic compound.

Alternatively, structure directing agents may be removed using oxidation processes, such as the oxidization of organic compounds using ozone. Ozone can also be used to remove organic structure directing agents at either room temperature or elevated temperatures, such as between 75° C. and 250° C., preferably at temperatures between 125° C. and 225° C., which can prevent severe degradation of the molecular sieve framework.

Characterization of the Molecular Sieve

In its as-synthesized form and on an anhydrous basis, the crystalline molecular sieve disclosed herein can be represented by the following empirical formula:

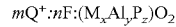

$$mQ^+:nF:(M_xAl_yP_z)O_2$$

wherein: (1) $Q^+$ represents a cation selected from the group consisting of 1,3-diisopropylimidazolium, 1,3-diisobutylimidazolium, and 1-isopropyl-3-isobutylimidazolium; (2) m is the number of moles of $Q^+$ per mole of $(M_xAl_yP_z)O_2$, and $0 < m \leq 1$; (3) n is the number of moles of fluoride ions per mole of $(M_xAl_yP_z)O_2$, and $0 < n \leq 1$; (4) M is a metal selected from zinc or a combination of zinc and silicon; (5) x is the mole fraction of M as tetrahedral oxides, and $0 < x \leq 0.5$; (6) y is the mole fraction of Al as tetrahedral oxides, and $y > 0$; (7) z is the mole fraction of P as tetrahedral oxides, and $z > 0$; and (8) $x+y+z=1$.

In embodiments, m has a value of from 0.01 to 1 (e.g., from 0.01 to 0.5, or from 0.01 to 0.3). In embodiments, n has a value of from 0.01 to 1 (e.g., from 0.1 to 0.8, or from 0.2 to 0.6).

In an embodiment, x has a value of from 0.001 to 0.5.

In an embodiment, x has a value of from 0.01 to 0.25, y has a value of from 0.3 to 0.7, and z has a value of from 0.25 to 0.7. In an embodiment, x has a value of from 0.01 to 0.15, y has a value of from 0.4 to 0.6, and z has a value of from 0.3 to 0.6.

Molecular sieves made by the process described herein are characterized by their XRD pattern. The X-ray diffraction pattern lines of Table 2 are representative of as-synthesized SSZ-90 made in accordance with this disclosure.

TABLE 2

Characteristic Peaks for As-Synthesized SSZ-90

| 2-Theta[a] | d-Spacing, nm | Relative Intensity[b] |
|---|---|---|
| 4.59 | 1.922 | W |
| 6.16 | 1.434 | M |
| 7.92 | 1.115 | VS |
| 8.24 | 1.072 | S |
| 10.02 | 0.882 | M |
| 11.44 | 0.773 | W |
| 12.13 | 0.729 | W |
| 14.69 | 0.603 | W |
| 15.44 | 0.573 | W |
| 15.90 | 0.557 | W |
| 16.54 | 0.536 | W |
| 17.22 | 0.515 | W |
| 18.38 | 0.482 | W |
| 20.58 | 0.431 | M |
| 21.10 | 0.421 | S |

[a] ±0.20 degrees
[b] The powder XRD patterns provided are based on a relative intensity scale in which the strongest line in the X-ray pattern is assigned a value of 100: W = weak (>0 to ≤20); M = medium (>20 to ≤40); S = strong (>40 to ≤60); VS = very strong (>60 to ≤100).

Minor variations in the diffraction pattern can result from variations in the mole ratios of the framework species of the particular sample due to changes in the lattice constants. In addition, sufficiently small crystals will affect the shape and intensity of peaks, leading to significant peak broadening. Minor variations can also result from variations in the organic compound used in the preparation. Notwithstanding these minor perturbations, the basic crystal lattice remains unchanged.

The powder X-ray diffraction patterns presented herein were collected by standard techniques. The radiation was CuKα radiation. The peak heights and the positions, as a function of 2θ where θ is the Bragg angle, were read from the relative intensities of the peaks (adjusting for background), and d, the interplanar spacing corresponding to the recorded lines, can be calculated.

Processes Using the Molecular Sieve

SSZ-90 may be used as an adsorbent, such as for separating at least one component from a mixture of components in the vapor or liquid phase having differential sorption characteristics with respect to the SSZ-90 molecular sieve of this disclosure. Therefore, at least one component can be partially or substantially totally separated from a mixture of components having differential sorption characteristics with respect to the SSZ-90 molecular sieve of this disclosure by contacting the mixture with the SSZ-90 molecular sieve of this disclosure to selectively sorb the one component.

SSZ-90 may also be used as a catalyst to catalyze a wide variety of organic compound conversion processes. Examples of chemical conversion processes which are effectively catalyzed by the molecular sieve disclosed herein, by itself or in combination with one or more other catalytically active substances including other crystalline catalysts, include those requiring a catalyst with acid activity. Examples of organic conversion processes which may be catalyzed by SSZ-90 include cracking, hydrocracking, disproportionation, alkylation, oligomerization, and isomerization.

As in the case of many catalysts, SSZ-90 can be incorporated with another material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with SSZ-90 (i.e., combined therewith or present during synthesis of the molecular sieve) which is active, tends to change the conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. The materials (i.e., clays, oxides, etc.) function as binders for the catalyst. It is desirable to provide a catalyst having good crush strength because in commercial use it is desirable to prevent the catalyst from breaking down into powder-like materials. These clay binders have been employed normally only for the purpose of improving the crush strength of the catalyst.

Naturally occurring clays which can be composited with the new crystal include the montmorillonite and kaolin family, which families include the sub-bentonites, and the kaolins commonly known as Dixie, McNamee, Ga. and Florida clays or others in which the main mineral constituent is halloysite, kaolinite, dictite, narcite, or anauxite. Such clays can be used in the raw state as originally mined or initially subjected to calcination, treatment or chemical modification. Binders useful for compositing with SSZ-90 also include inorganic oxides, notably alumina.

In addition to the foregoing materials, SSZ-90 can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of SSZ-90 crystalline molecular sieve and inorganic oxide matrix vary widely, with the SSZ-90 content ranging from 1 to 99 wt. % of the composite and more usually in the range of from 20 to 80 wt. % of the composite.

EXAMPLES

The following illustrative examples are intended to be non-limiting.

Example 1

Synthesis of 1,3-Diisobutylimidazolium Bromide 1,3-Diisobutylimidazolium hydroxide was prepared as described by R. H Archer et al. (*Chem. Mater.* 2010, 22, 2563-2572). 6.5 g of hydrobromic acid (48%) was slowly added to 80 g of 1,3-diisobutylimidazolium hydroxide (9%) and allowed to stir overnight at room temperature. Water was removed in vacuo and the solids dried with flowing nitrogen before storing in a vacuum oven at room temperature.

Example 2

Synthesis of ZnAPO SSZ-90

Using 1,3-Diisobutylimidazolium Bromide 156 mg of aluminum isopropoxide (140 mesh), 159 mg of zinc acetate dihydrate, 1.92 g of 1,3-diisobutylimidazolium bromide, 172 mg of concentrated phosphoric acid, and 0.02 g of concentrated HF (50%) were added to a PEEK reactor liner and mixed with a plastic stirrer. The liner was then capped and placed within a Parr steel autoclave reactor. The autoclave was placed in an oven and heated at 160° C. for 3 days with tumbling (43 rpm). The products were recovered by vacuum filtration, washed with deionized water and dried at 95° C.

The resulting as-synthesized product was analyzed by powder XRD. The powder XRD pattern is shown in FIG. 1 and indicates that the product has the DFO framework type.

Example 3

Synthesis of ZnSAPO SSZ-90

Using 1,3-Diisobutylimidazolium Bromide 156 mg of aluminum isopropoxide (140 mesh), 159 mg of zinc acetate dihydrate, 1.9 g of 1,3-diisobutylimidazolium bromide, 16 mg of tetraethyl orthosilicate, 185 mg of concentrated phosphoric acid, and 0.02 g of concentrated HF (50%) were added to a PEEK reactor liner and mixed with a plastic stirrer. The liner was then capped and placed within a Parr steel autoclave reactor. The autoclave was placed in an oven and heated at 160° C. for 6 days with tumbling (43 rpm). The products were recovered by vacuum filtration, washed with deionized water and dried at 95° C.

The resulting as-synthesized product was analyzed by powder XRD and indicated that the product has the DFO framework type.

Example 4

Synthesis of ZnAPO SSZ-90

Using 1-Isopropyl-3-isobutylimidazolium Bromide 110 mg of aluminum isopropoxide (140 mesh), 185 mg of zinc acetate ehydrate, 2.13 g of 1-isopropyl-3-isobutylimidazolium bromide, 200 mg of concentrated phosphoric acid, and 0.02 g of concentrated HF (50%) were added to a PEEK reactor liner and mixed with a plastic stirrer. The liner was then capped and placed within a Parr steel autoclave reactor. The autoclave was placed in an oven and heated at 160° C. for 3 days with tumbling (43 rpm). The products were recovered by vacuum filtration, washed with deionized water and dried at 95° C.

Figure 2:
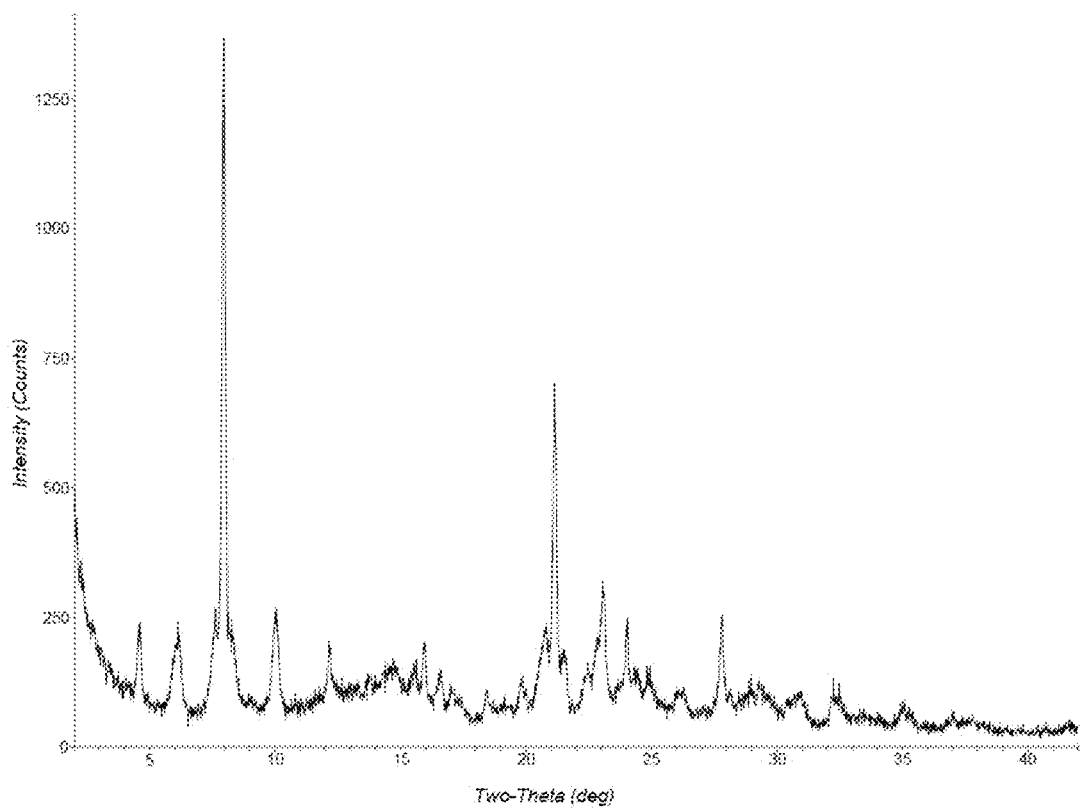
FIG. 2 is a powder XRD pattern of the as-synthesized ZnAPO molecular sieve prepared in Example 4.

The resulting as-synthesized product was analyzed by powder XRD. The powder XRD pattern is shown in FIG. 2 and indicates that the product has the DFO framework type.

Example 5

Synthesis of ZnAPO SSZ-90

Using 1,3-Diisopropylimidazolium Bromide 1.15 g of aluminum isopropoxide (140 mesh), 0.42 g of zinc acetate dihydrate, 4.5 g of 1,3-diisopropylimidazolium bromide, 0.89 g of concentrated phosphoric acid, and 0.06 g of concentrated HF (50%) were added to a Teflon liner and mixed with a plastic stirrer. The liner was then capped and placed within a Parr steel autoclave reactor. The autoclave was placed in an oven and heated at 160° C. for 3 days with tumbling (43 rpm). The products were recovered by vacuum filtration, washed with deionized water and dried at 95° C.

Figure 3:
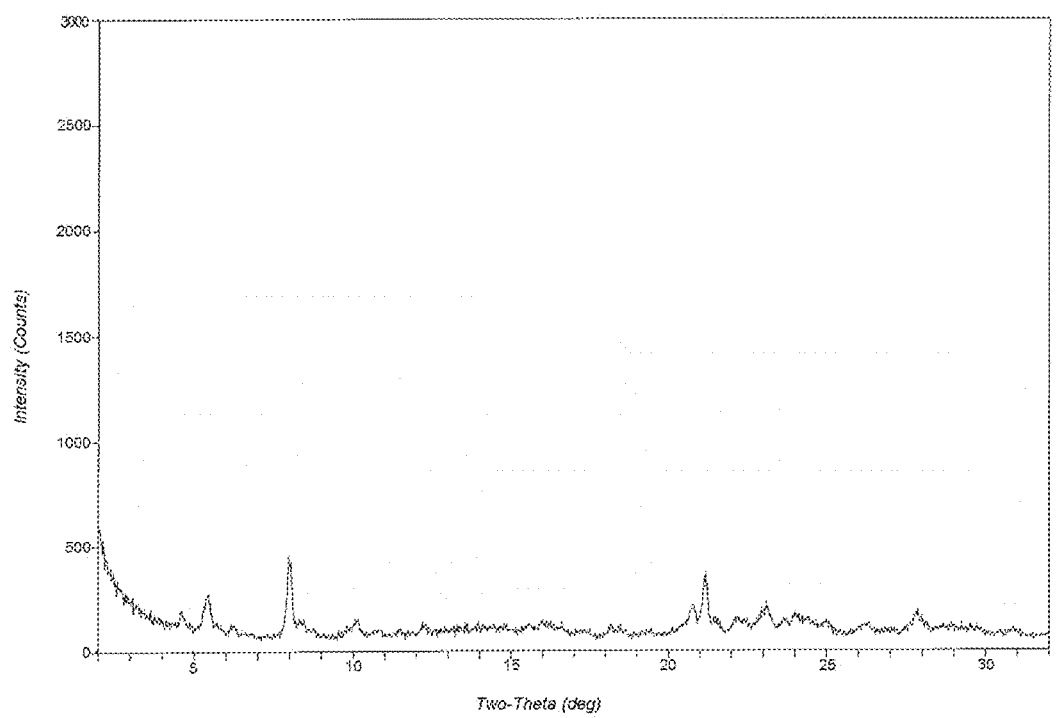
FIG. 3 is a powder XRD pattern of the as-synthesized ZnAPO molecular sieve prepared in Example 5.

The resulting as-synthesized product was analyzed by powder XRD. The powder XRD pattern is shown in FIG. 3 and indicates that the product has the DFO framework type.

Example 6

Ozonolysis of As-Synthesized ZnSAPO SSZ-90

The as-synthesized product of Example 3 was ground and placed inside a pipette within a heated copper pipe with an oxygen feed at a rate of about 125 mL/min. The material was heated from ambient temperature to 200° C. and held for 12 hours in the presence of about 1.82% ozone. The powder was quickly sealed in a separate vial and stored in a moisture-free environment.

Thermogravimetric analysis and $^{13}C$ NMR indicated essentially complete removal of carbonaceous material from the molecular sieve after the treatment with ozone (i.e., residual organic compounds well below 1% of the original content).

Figure 4:
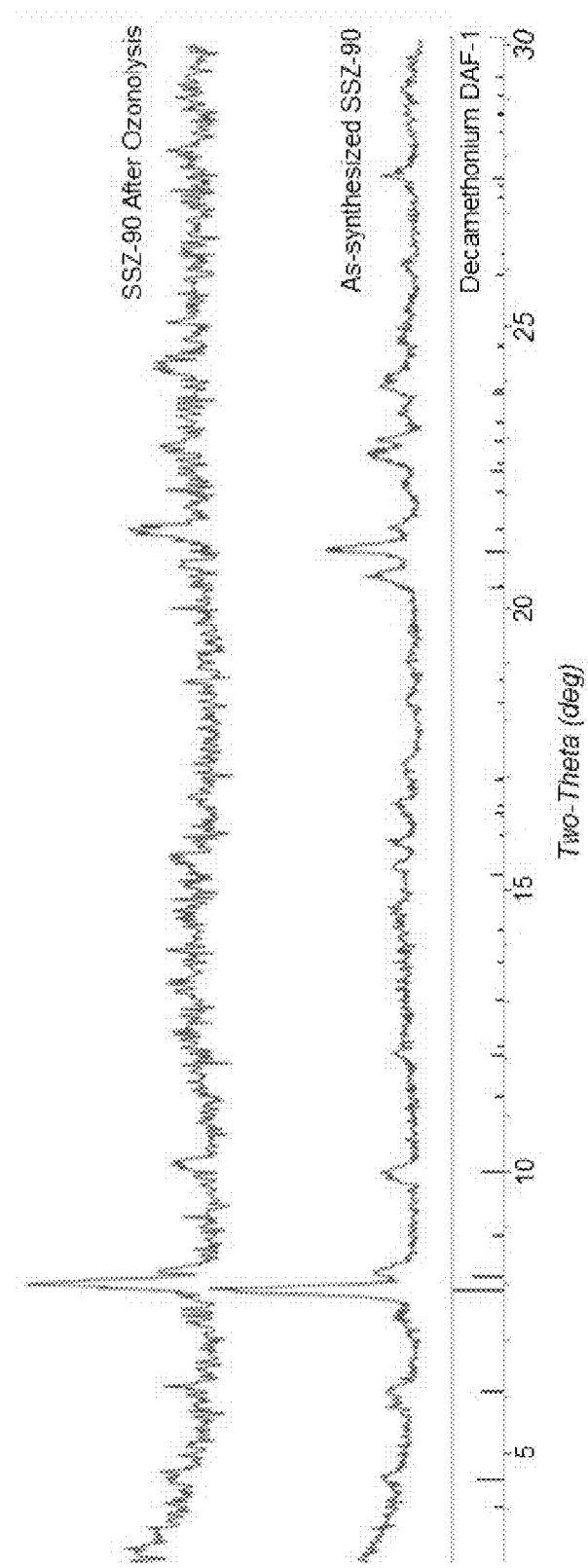
FIG. 4 illustrates a comparison of three X-ray diffraction patterns, the top one being ZnSAPO SSZ-90 after treatment with ozone to remove the structure directing agent, the middle one being as-synthesized ZnSAPO SSZ-90, and the bottom one being as-synthesized DAF-1.

FIG. 4 shows a comparison of three X-ray diffraction patterns, the top one being SSZ-90 after treatment with ozone to remove the structure directing agent (SDA), the middle one being as-synthesized SSZ-90, and the bottom one being as-synthesized DAF-1. Powder XRD indicates that the sample remains crystalline after treatment with ozone.

Figure 5:
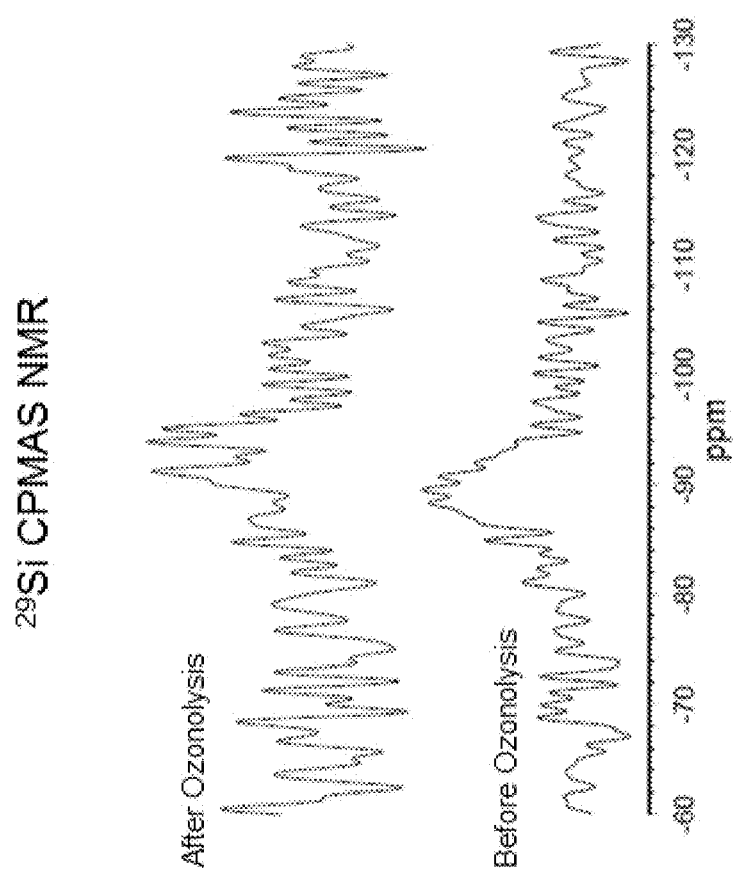
FIG. 5 illustrates the $^{29}$Si CPMAS NMR of ZnSAPO SSZ-90 after ozonolysis compared with ZnSAPO SSZ-90 before ozonolysis.

The zinc silicoaluminophosphate molecular sieve was also characterized by $^{29}Si$ CPMAS NMR. FIG. 5 illustrates the $^{29}Si$ CPMAS NMR of zinc silicoaluminophosphate SSZ-90 after ozonolysis compared with zinc silicoaluminophosphate SSZ-90 before ozonolysis. A signal at about −89 ppm, which is typical for Si islands of SAPO material, is observed. The overall position and line shape of the peak appears nearly similar after SDA removal by ozonolysis.

Figure 6:
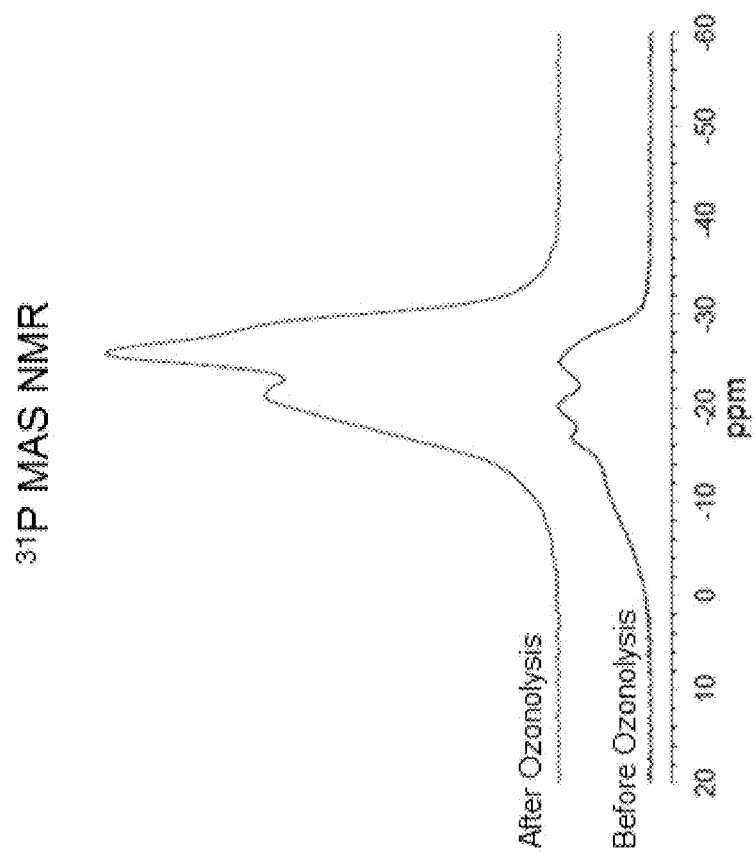
FIG. 6 illustrates the $^{31}$P MAS NMR of ZnSAPO SSZ-90 after ozonolysis compared with ZnSAPO SSZ-90 before ozonolysis.
Figure 7:
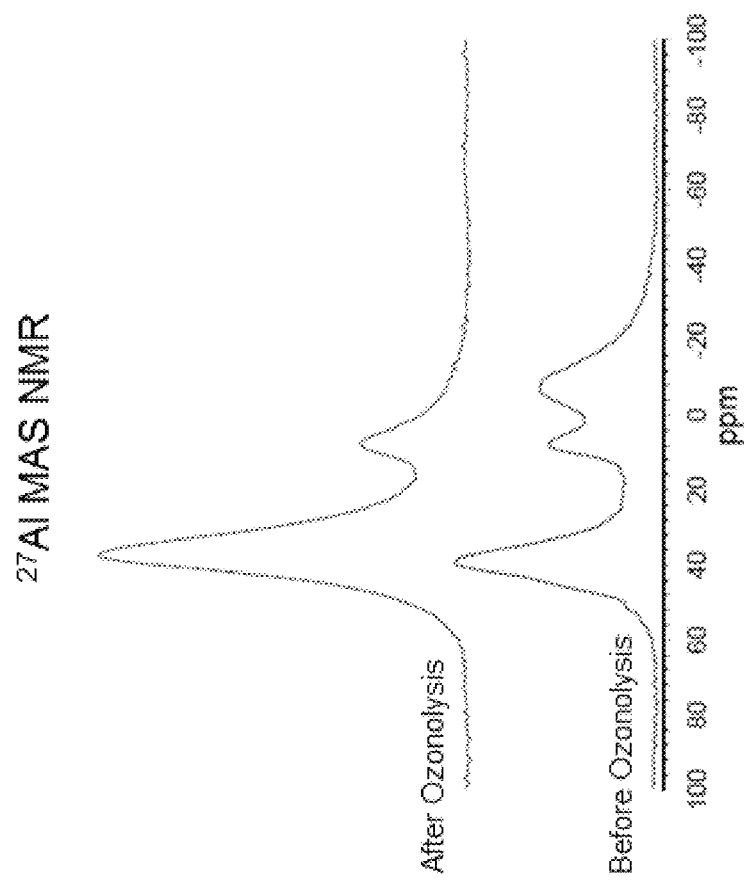
FIG. 7 illustrates the $^{27}$Al MAS NMR of ZnSAPO SSZ-90 after ozonolysis compared with ZnSAPO SSZ-90 before ozonolysis.

The zinc silicoaluminophosphate molecular sieve was further characterized by $^{31}P$ MAS NMR, which is shown in FIG. 6, and by $^{27}Al$ MAS NMR which is shown in FIG. 7. In FIGS. 6 and 7, a comparison is shown between the zinc silicoaluminophosphate before and after ozonolysis. FIGS. 6 and 7 show the conversion of octahedral centers after ozonolysis to form more $PO_4$ and $AlO_4$, respectively.

After removal of the SDA cation, the molecular sieve was subjected to a surface area and micropore analysis using nitrogen as adsorbate and via the BET method. The molecular sieve had a BET surface area of 311 $m^2/g$, a micropore volume of 0.099 $cm^3/g$, and a total pore volume of 0.711 $cm^3/g$.

Example 7

Preparation of Pt-Exchanged ZnSAPO SSZ-90

346 mg of ZnSAPO SSZ-90 as prepared in Example 6 was dried in a vacuum line at 132° C. for 2 hours under a vacuum of about 30 mm Torr. Then, 5 mg of platinum(II) acetylacetonate dissolved in 365 mg of toluene was added to a bottle containing SSZ-90 for incipient wetness impregnation. The resulting mixture was vigorously stirred with a spatula for 5 minutes and then kept in the closed bottle at room temperature for 1 day. The resulting Pt/SSZ-90 catalyst was then dried in a vacuum oven under a vacuum of −20 inch Hg and a temperature of 230° F. for 2 hours. Subsequently, the Pt/SSZ-90 catalyst was calcined in a calcination oven in a flow of dry air with the following temperature program: from room temperature to 120° C. in 30 minutes, then held at 120° C. for 30 minutes, subsequently heated from 120° C. to 350° C. in 1 hour, then held at 350° C. for 3 hours before allowing to cool down to room temperature.

Example 8

Hexane Conversion Over Pt/SSZ-90

Platinum-exchanged SSZ-90 as prepared in Example 7 was pelletized at 3 kpsi, crushed and granulated to 20-40 mesh, and loaded into the center of a stainless steel tube reactor. The catalyst was then pre-treated in a hydrogen flow at atmospheric pressure with the following temperature program: from room temperature to 400° F. (204° C.) in 2 hours, then held at 400° F. for 1 hour, subsequently heated from 400° F. to 800° F. (427° C.) in 3 hours, and held at 800° F. for 8 hours before adjusted to a preselected reaction temperature such as 950° F. (510° C.).

Hydroprocessing of n-hexane over the Pt/SSZ-90 catalyst was conducted under the following conditions: a reaction temperature of 950° F., a pressure of 80 psig, a liquid hourly space velocity of 1.5 $h^-$, and a $H_2$/n-hexane mole ratio at the reactor inlet of 5:1. The results are set forth in Table 3.

TABLE 3

| Conversion of n-hexane, wt. % | 34.04 |
|---|---|
| Yield, wt. % | |
| Methane | 1.59 |
| Ethane | 4.07 |
| Ethylene | 1.28 |
| Propane | 7.04 |
| Propylene | 4.31 |
| i-Butane | 0.72 |
| n-Butane | 1.52 |
| Butenes | 2.66 |
| i-Pentane | 0.47 |
| n-Pentane | 0.34 |
| Pentenes | 0.94 |
| 2,2-Dimethylbutane | 0.06 |
| 2,3-Dimethylbutane | 0.59 |
| 2-Methylpentane | 2.46 |
| 3-Methylpentane | 1.88 |

TABLE 3-continued

| Hexenes | 1.59 |
|---|---|
| Methylcyclopentane | 0.37 |
| Benzene | 0.50 |
| Unknowns | 1.65 |

A noticeably large amount of olefins (1.28 wt. % ethylene, 4.31 wt. % propylene, 2.66 wt. % butenes, 0.94 wt. % pentenes and 1.59 wt. % hexenes) was produced at a n-hexane conversion of 34.04 wt. %, leading to a total olefin yield of 10.78 wt. % which corresponds to a selectivity of 31.67 wt. %. It is especially noteworthy to point out the relatively high olefin-to-paraffin ratios of $C_2$ and $C_3$ products The singular forms "a," "an," and "the" include plural referents unless the context clearly dictates otherwise.

The disclosure of all patents, patent applications, and publications cited in the disclosure are hereby incorporated by reference, to the extent that they provide exemplary, procedural or other details supplementary to the disclosure.

The invention claimed is:

1. A crystalline molecular sieve comprising $[ZnO_4]$, $[AlO_4]$ and $[PO_4]$ corner-sharing tetrahedral units and having the DFO framework type.

2. The molecular sieve of claim 1, further comprising $[SiO_4]$ corner-sharing tetrahedral units.

3. The molecular sieve of claim 1, having, in its as-synthesized form, an X-ray diffraction pattern substantially as shown in the following table:

| 2-Theta | d-Spacing, nm | Relative Intensity |
|---|---|---|
| 4.59 ± 0.20 | 1.922 | W |
| 6.16 ± 0.20 | 1.434 | M |
| 7.92 ± 0.20 | 1.115 | VS |
| 8.24 ± 0.20 | 1.072 | S |
| 10.02 ± 0.20 | 0.882 | M |
| 11.44 ± 0.20 | 0.773 | W |
| 12.13 ± 0.20 | 0.729 | W |
| 14.69 ± 0.20 | 0.603 | W |
| 15.44 ± 0.20 | 0.573 | W |
| 15.90 ± 0.20 | 0.557 | W |
| 16.54 ± 0.20 | 0.536 | W |
| 17.22 ± 0.20 | 0.515 | W |
| 18.38 ± 0.20 | 0.482 | W |
| 20.58 ± 0.20 | 0.431 | M |
| 21.10 ± 0.20 | 0.421 | S. |

4. The molecular sieve of claim 1, wherein the molecular sieve, in its as-synthesized form and on an anhydrous basis, is represented by the empirical formula:

$$mQ^+:nF:(M_xAl_yP_z)O_2$$

wherein:
(1) $Q^+$ represents a cation selected from the group consisting of 1,3-diisopropylimidazolium, 1,3-diisobutylimidazolium, and 1-isopropyl-3-isobutylimidazolium;
(2) m is the number of moles of $Q^+$ per mole of $(M_xAl_yP_z)O_2$, and $0<m\leq1$;
(3) n is the number of moles of fluoride ions per mole of $(M_xAl_yP_z)O_2$, and $0<n\leq1$;
(4) M is a metal selected from zinc or a combination of zinc and silicon;
(5) x is the mole fraction of M as tetrahedral oxides, and $0<x\leq0.5$;
(6) y is the mole fraction of Al as tetrahedral oxides, and y>0;

(7) z is the mole fraction of P as tetrahedral oxides, and z>0; and (8) x+y+z=1.

5. The molecular sieve of claim 4, wherein M is zinc.

6. The molecular sieve of claim 4, wherein M is a combination of zinc and silicon.

7. The molecular sieve of claim 4, wherein m has a value of from 0.01 to 0.5.

8. The molecular sieve of claim 4, wherein n has a value of from 0.2 to 0.6.

9. The molecular sieve of claim 4, wherein x has a value of from 0.01 to 0.25, y has a value of from 0.3 to 0.7, and z has a value of from 0.25 to 0.7.

10. A method for preparing a crystalline molecular sieve comprising [$ZnO_4$], [$AlO_4$] and [$PO_4$] corner-sharing tetrahedral units and having the DFO framework type, the method comprising:

(a) preparing a reaction mixture containing:

(1) at least one source of zinc;

(2) optionally, at least one source of silicon;

(3) at least one source of aluminum;

(4) at least one source of phosphorus;

(5) fluoride ions; and (6) an ionic liquid [$Q^+A^-$] comprising a cation ($Q^+$) selected from the group consisting of 1,3-diisopropylimidazolium, 1,3-diisobutylimidazolium, and 1-isopropyl-3-isobutylimidazolium; and an anion ($A^-$) which is not detrimental to the formation of the molecular sieve; and (b) maintaining the reaction mixture under crystallization conditions sufficient to form crystals of the molecular sieve.

11. The method of claim 10, wherein the reaction mixture comprises, in terms of mole ratios, the following:

| | |
|---|---|
| $ZnO/Al_2O_3$ | 0.05 to 1.5 |
| $SiO_2/Al_2O_3$ | 0 to 0.90 |
| $P_2O_5/Al_2O_3$ | 0.50 to 1.50 |
| $F/Al_2O_3$ | 0.25 to 0.75 |
| [$Q^+A^-$/$Al_2O_3$] | 5 to 100. |

12. The method of claim 10, wherein the reaction mixture comprises, in terms of mole ratios, the following:

| | |
|---|---|
| $ZnO/Al_2O_3$ | 0.1 to 1.0 |
| $SiO_2/Al_2O_3$ | 0.05 to 0.70 |
| $P_2O_5/Al_2O_3$ | 0.80 to 1.20 |
| $F/Al_2O_3$ | 0.25 to 0.75 |
| [$Q^+A^-$/$Al_2O_3$] | 5 to 40. |

13. The method of claim 10, wherein the anion ($A^-$) is selected from the group consisting of halides, acetates, phosphates, phosphinates, aluminates, borates, sulfates, sulfonates, imides, amides, and cyanates.

14. The method of claim 10, wherein the crystallization conditions include a temperature of from 100° C. to 200° C.

15. The method of claim 10, wherein the molecular sieve has, in its as-synthesized form, an X-ray diffraction pattern substantially as shown in the following table:

| 2-Theta | d-Spacing, nm | Relative Intensity |
|---|---|---|
| 4.59 ± 0.20 | 1.922 | W |
| 6.16 ± 0.20 | 1.434 | M |
| 7.92 ± 0.20 | 1.115 | VS |
| 8.24 ± 0.20 | 1.072 | S |
| 10.02 ± 0.20 | 0.882 | M |
| 11.44 ± 0.20 | 0.773 | W |
| 12.13 ± 0.20 | 0.729 | W |
| 14.69 ± 0.20 | 0.603 | W |
| 15.44 ± 0.20 | 0.573 | W |
| 15.90 ± 0.20 | 0.557 | W |
| 16.54 ± 0.20 | 0.536 | W |
| 17.22 ± 0.20 | 0.515 | W |
| 18.38 ± 0.20 | 0.482 | W |
| 20.58 ± 0.20 | 0.431 | M |
| 21.10 ± 0.20 | 0.421 | S. |

16. A process for converting a feedstock comprising an organic compound to a conversion product which comprises the step of contacting the feedstock with a catalyst, at organic compound conversion conditions, the catalyst comprising an active form of the molecular sieve of claim 1.

17. The process of claim 16, wherein the process is selected from cracking, hydrocracking, disproportionation, alkylation, oligomerization, and isomerization.

* * * * *